Figure 1:
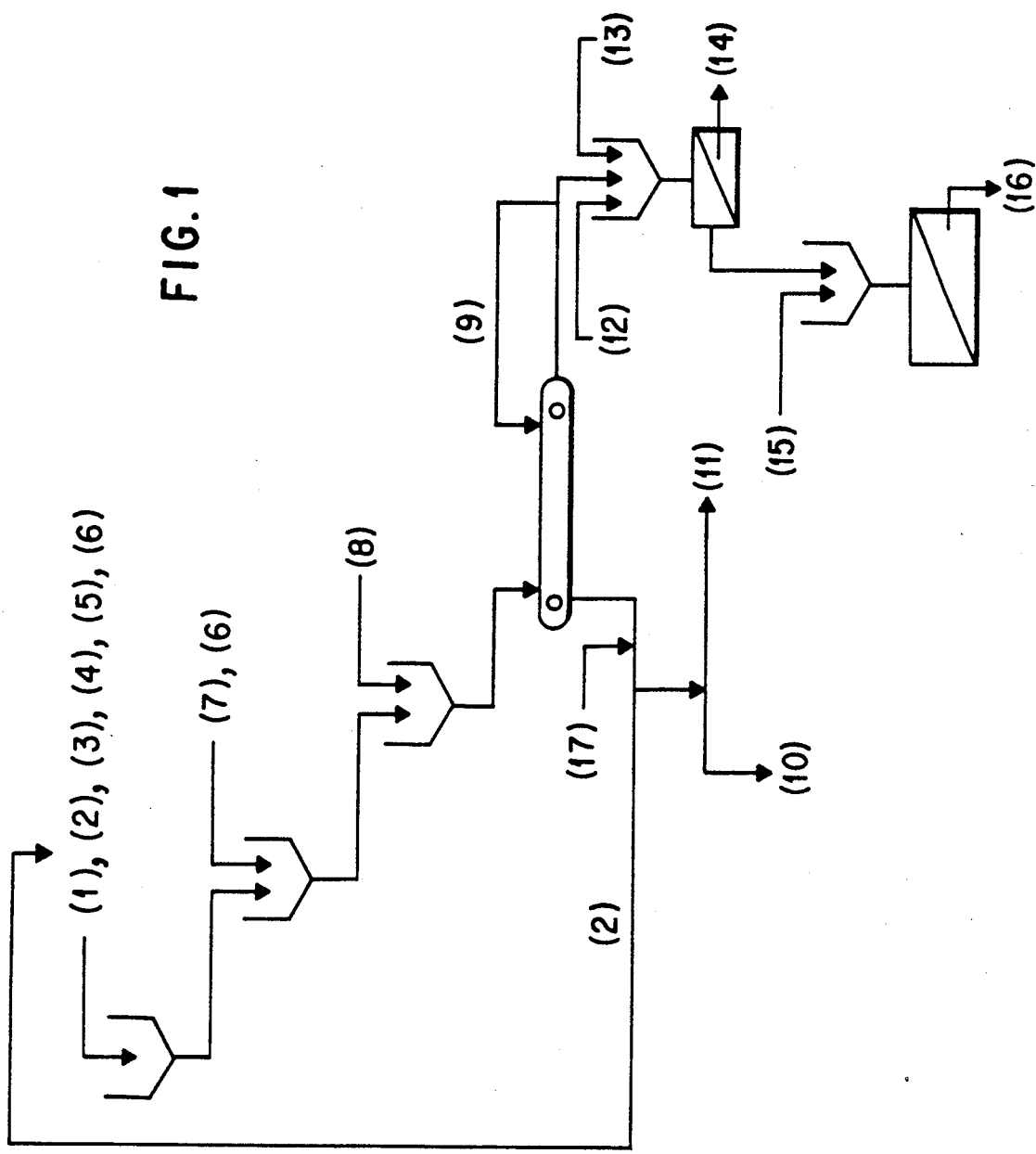

| United States Patent [19] | [11] Patent Number: 4,997,979 |
| Coste et al. | [45] Date of Patent: Mar. 5, 1991 |

[54] PROCESS FOR THE PREPARATION OF ALKALINE PHENYLPYRUVATE

[75] Inventors: Phillippe Coste, Villeurbanne; Michel Baudoin, Craponne; Philippe Leconte, Lyons; Robert Perron, Charly, all of France

[73] Assignee: Rhone-Poulenc Chimie, Courbevoie Cedex, France

[21] Appl. No.: 332,723

[22] Filed: Apr. 4, 1989

[30] Foreign Application Priority Data

Apr. 6, 1988 [FR] France ................................ 88 04515

[51] Int. Cl.$^5$ ............................................... C07C 51/10
[52] U.S. Cl. ................................................... 562/406
[58] Field of Search ........................................ 562/406

[56] References Cited

U.S. PATENT DOCUMENTS 4,152,352  5/1979  Perron .................................. 562/406
4,576,809  3/1986  Gauthier-Lafaye ................. 562/406

*Primary Examiner*—Michael L. Shippen
*Attorney, Agent, or Firm*—Finnegan, Henderson, Farabow, Garrett, and Dunner

[57] ABSTRACT

A process for the preparation of alkaline phenylpyruvate by carbonylation of benxzyl chloride in the presence of a cobalt catalyst. The alkaline phenylpyruvate is useful as an intermediate in the preparation of phenylalanine.

25 Claims, 1 Drawing Sheet

PROCESS FOR THE PREPARATION OF ALKALINE PHENYLPYROVATE

The present invention relates to a new process for the preparation of alkaline phenylpyruvate by double carbonylation of benzyl chloride. It relates more particularly to an industrial process for the preparation of the alkaline phenylpyruvate.

It is known to prepare phenylpyruvates by double carbonylation of benzyl chloride. U.S. Pat. No. 4,152,352 describes a process for the preparation of phenylpyruvic acid by double carbonylation of benzyl chloride in the presence of a cobalt carbonyl-based catalyst, a basic agent and, particularly, an alkaline-earth metal base in a water-alcohol solvent.

The preparation of the catalyst, which is a cobalt tetracarbonyl salt, has been described in detail in European Patent No. 108,698. According to this patent, cobalt dichloride, a sulfur derivative or a mixture of sulfur derivatives are brought into contact with an alkaline-earth metal base, preferably lime, in a medium consisting of water and/or an alcohol.

Taken together these two patents describe the preparation of the catalyst, which unfortunately has to be stored, and its subsequent use in the double carbonylation. Neither patent teaches nor suggests both the preparation of the catalyst and carbonylation of benzyl chloride in a single reaction entity to produce calcium phenylpyruvate by a process that is easy to implement and which gives good yields.

Such a process, although simple in principle, poses a great many problems of implementation. On the one hand, the reaction medium contains three phases (solid, liquid and gas), thus, requiring technology adapted to the stirring and gas-liquid transfer. Also, the kinetics of the reaction must be fast. In addition, since the phenylpyruvate products pose serious difficulties with regard to separating these products from the complex reaction medium, which contains inorganic salts, organic products, solvents and water, the recovery of the phenylpyruvate is extremely complicated.

The calcium phenylpyruvate obtained, moreover, is a fragile product. It cannot be heated for fear of degradation nor, due to its physical form (i.e., crystals and needles of small size), can it be distilled or extracted in pure form by any solvent. Filtration is the only profitable industrial technique by which it is possible to separate the phenylpyruvate. The filtration depends very much on the conditions of the preparation of the phenylpyruvate and, thus, on the physical and chemical qualities which characterize the phenylpyruvate following double carbonylation.

Insofar as an economical and profitable process is desired, the secondary products, such as solvents and inorganic salts, should be recycled or eliminated, taking into account all environmental safety standards.

The calcium phenylpyruvate obtained must be subjected to a transsalification reaction to obtain an alkaline phenylpyruvate which is then used as an intermediate in the pharmaceutical or plant protection industry. The principal use of alkaline phenylpyruvate is the preparation of phenylalanine.

The synthesis of phenylalanine is advantageously carried out by enzymatic transamination, such as described, for example, in U.S. Pat No. 4,600,692. Since such an enzymatic reaction is promoted by the degree of purity of the raw materials, it is desirable to obtain an alkaline phenylpyruvate of high purity. All of the problems discussed above can be solved by the process of the present invention.

It is an object of the present invention to obtain a reaction solution from which it is possible to isolate calcium phenylpyruvate by filtration, and to subsequently convert it to alkaline phenylpyruvate.

FIG. 1 represents a flow diagram of the process of the present invention.

The present invention relates to a process for the preparation of alkaline phenylpyruvate comprising:

bringing a suspension of calcium hydroxide (1) in a water/alcohol mixture (2) into contact with a sulfide (3), a thiosulfate (4), an inorganic cobalt salt (5) and carbon monoxide (6) in a reactor;

introducing benzyl chloride (7) into the resultant mixture while maintaining the reactor under carbon monoxide pressure;

forming calcium phenylpyruvate;

filtering the calcium phenylpyruvate;

drying the calcium phenylpyruvate at a temperature effective to eliminate the alcohol;

acidifying a suspension of the calcium phenylpyruvate in a water-immiscible organic solvent;

isolating the acidified phenylpyruvate; and neutralizing the acidified phenylpyruvate with an alkaline base.

It is not suggested, from a reading of the patents directed to the preparation of the double carbonylation catalyst (e.g., EP No. 108,698), to prepare the carbonylation catalyst in situ in the carbonylation reactor and to add the benzyl chloride directly into the reactor. Rather, these patents separately prepare the catalyst in a different reactor and then add the prepared catalysts to the benzyl chloride.

The process of the present invention advantageously avoids the prior preparation of the catalyst in another reactor and its subsequent storage and handling. It should be remembered that calcium cobalt tetracarbonyl is a dangerous non-volatile product and that its conversion to tetracarbonylhydrido cobalt is a volatile product of extreme toxicity. From the point of view of economy, the advantage of using only one reactor is considerable, since it avoids successively maintaining the pressure in two reactors with carbon monoxide.

The sulfide and thiosulfate are preferably in the form of salts such as sodium sulfide or sodium thiosulfate.

The filtration problems associated with calcium phenylpyruvate have been solved by working with several chemical or technological parameters.

From a chemical point of view, to facilitate the filtration of the calcium phenylpyruvate, it as been discovered that the cobalt concentration in the reaction medium should be as low as possible. It is preferable to use a concentration of cobalt catalyst per liter of reaction medium ranging from about $10^{-3}$ to $5 \times 10^{-3}$ mole/liter. A concentration of about $10^{-3}$ mole/liter is highly preferred.

This reduction in the concentration of cobalt tetracarbonyl makes it possible to maintain an appropriate reaction rate on an industrial scale. No document in the prior art discloses a carbonylation with such a small quantity of catalyst.

From a technological point of view, the stirring system has an effect on the filterability. The larger the phenylpyruvate crystals, the easier the filterability. Preferably, the stirring system must provide for the best gas-liquid contact, but must destroy as few crystals as possible. The preferred system used in the present invention comprises a propeller requiring low stirring power and a gas circulator which circulates the gaseous atmosphere of the reactor in the reaction medium.

The solvent also plays an important role with regard to the filterability. Alcohol promotes the filterability and selectivity, and water promotes the reaction rate. The alcohol is preferably isopropanol. The best reaction rate/filterability compromise was obtained with a water/isopropanol ratio containing about 20 volumes of water to 80 volumes of isopropanol.

It is preferred to use a molar concentration of cobalt per liter of reaction medium of $1 \times 10^{-3}$ to $5 \times 10^{-3}$ gram-atom/ liter, a quantity of calcium hydroxide preferably corresponding to the stoichiometric amount, a combined quantity of sulfide and thiosulfate expressed in moles per gram-atom of cobalt of from about 0.01:1 to 1:1 and, more preferably, about 0.2:1. It is preferred to work with a molar ratio of cobalt catalyst to benzyl chloride of from about $1 \times 10^{-3}$:1 to $1 \times 10^{-2}$:1. It is advantageous to use the carbon monoxide at a pressure of from about 5 to 30 bar. The double carbonylation reaction is preferably carried out at a temperature of from about 60° to 90° C.

Before filtering the reaction medium, it is preferred to carry out a detoxification stage to convert all the cobalt remaining in the oxidation state $(-1)$ to the oxidation state $(+2)$. This oxidation step is preferably carried out in the presence of sodium hypochlorite. A 10% aqueous solution of sodium hypochlorite (8) is preferred. The solution is preferably introduced into the crude reaction medium at an elevated temperature of preferably about 60° C.

The suspension thus obtained does not contain any cobalt in the oxidation state $(-1)$, and further, has a rheology which is unmodified relative to the suspension resulting from the reaction, without modification of the reaction components apart from the oxidation of the cobalt.

In the filtration step, the suspension can be filtered through a thin filter, such as a band filter, or any other device which avoids forming a cake having too great a thickness. The filtration is preferably carried out at an elevated temperature of about 60° C.

The filtration residue is washed with a water/ carbonylation, preferably containing one volume of water for one volume of alcohol (9). The alcohol is preferably isopropanol. The washing is preferably carried out by elution so as not to cause turbulence at the level of the solid or at the level of the liquid, but to displace only the mother liquors of the initial solution.

The filtrate contains a water/alcohol azeotropic mixture that is recovered by distillation after acidification of the filtrate and recycled to the contacting step. This acidification is carried out up to a pH of about 3. It is effected, for example, by using a mineral acid (17) selected from hydrochloric acid and sulfuric acid.

This makes it possible to release the acids, by-products of the reaction, from their calcium salts (11). The acids then take the form of a liquid oil which does not disturb the distillation of the azeotrope, and which, moreover, prevents the problems of soiling of the column.

The filtration residue is then dried at a temperature effective to eliminate the remaining alcohol, preferably at a temperature of less than or equal to 80° C. It is preferable to allow a quantity of residual water to remain so as not to degrade the calcium phenylpyruvate. This quantity of water is preferably from about 5 to 20% by weight.

The dried calcium phenylpyruvate is acidified to release the phenylpyruvic acid in an organic solution and to release the salts in an aqueous solution, particularly the cobalt and calcium chlorides.

This acidification reaction is preferably carried out under precise conditions to be able to easily separate the acid, preferably by decantation. The calcium phenylpyruvate is preferably introduced in a water-immiscible organic solution (13) with an aqueous solution of hydrochloric acid (12).

The organic solvents are preferably selected from aliphatic or aromatic solvents, which solvents may be halogenated. Suitable solvents include chloroform, methylene chloride, chlorobenzenes, toluene, xylenes, as well as ethers, such as isopropyl ether, ethyl ether, and methyltert-butylether, and esters, such as ethyl acetate. It is preferable to use methyltert-butylether as the organic solvent.

The molar ratio between the quantity of hydrochloric acid introduced and the crude calcium phenylpyruvate of filtration is preferably between 2:1 and 8:1; it is more preferred to use a molar ratio of about 4:1. The weight of calcium phenylpyruvate to be used is preferably between 0.1 to 1 kg.

It is preferable to produce a methyltert-butylether and hydrochloric acid emulsion and to introduce into this emulsion the calcium phenylpyruvate. If the amount of water provided is too great, the appearance of a solid is observed. This solid disturbs the decantation and prevents the separation of the phenylpyruvic acid.

If the amount of water is too small, the phenylpyruvic acid deteriorates. The preferred amount of water, calculated relative to the solvent, is from about 1:1 to 3:1 according to a weight ratio.

After acidification, the phenylpyruvic acid in solution in the organic solvent is separated from the aqueous solution (14) containing the inorganic salts and the cobalt. The preferred method of separation is decantation.

This solution of phenylpyruvic acid in the organic solvent is salified by an aqueous solution of an alkaline base (15), preferably continuously, in a reactor equipped with, for example, a shearing stirrer. The alkaline solution is preferably sodium carbonate. The pH of the resultant solution is advantageously maintained between 6 and 8, and the dwell time is preferably less than 1 hour. After salification the alkaline phenylpyruvate in aqueous solution (16) is preferably separated from the immiscible organic solvent by decantation. The alkaline phenylpyruvate can be introduced directly for the enzymatic transamination reaction described above.

The present invention will be described more fully by means of the following examples which should not be regarded as limiting the invention.

EXAMPLE OF THE PREPARATION OF THE CALCIUM PHENYLPYRUVATE

1. Test with concentrated catalytic solution prepared at time of use.

The following were charged successively into a 3.6 liter stainless steel reactor equipped with a mixel propeller and gas circulator:
  222 g (3 mol) of $Ca(OH)_2$;
  1250 g of isopropanol; and
  311 g of water.

The suspension was stirred and purged with $3 \times 5$ bar of nitrogen and then by $3 \times 5$ bar of CO.

29.6 g of a water/alcohol solution of $[Co(CO)_4^-]_2Ca$, previously prepared according to European Patent No. 108,698 and containing $6 \times 10^{-3}$ moles of $Co^{-1}$, were then introduced. The reactor was brought to 70° C. under 19 bar of CO.

Then, 250 g of benzyl chloride were introduced at 70° under 19 bar of CO for a period of 6 hours. The $Co^{-1}$/benzyl chloride molar ratio was $3 \times 10^{-3}$.

At the end of the reaction (CO absorption of about 0), the pressure was reduced to 1 bar, the reaction mixture was cooled to 60° C., the cobalt was oxidized by addition of 100 g of a 10% NaOCl solution, and then the suspension was filtered and the residue washed with a 50/50 v/v $H_2O$/isopropanol mixture.

During filtration, a resistance to flow of 0.4 m/kg was measured.

After drying, a dry cake weighing 438 g and titrating 56.6% of phenylpyruvic acid was obtained. This corresponded to a yield of 77.4% relative to the benzyl chloride used. 2. Test with preparation of the catalyst in the reactor.

In the same apparatus as above there were charged successively:

| | |
|---|---|
| $Ca(OH)_2 =$ | 222 g (3 mol) |
| isopropanol = | 1240 g |
| water = | 311 g |
| $CoCl_2 =$ | 10.87 mmol |
| $Na_2S =$ | 0.95 mmol |
| $Na_2SO_3 =$ | 0.87 mmol |

The reactor was purged with $3 \times 5$ bar of nitrogen and then with $3 \times 5$ bar of CO.

The temperature was raised to 75° under 19 bar of CO, and the reaction was allowed to take place for 45 minutes. The yield of $Ca[Co(CO)_4]$ was estimated at about 80%. About 8 mmol of $Co^{-1}$ were thus in solution. Then, 245 g (1.937 moles) of benzyl chloride were introduced under pressure in the course of 20 minutes. The $Co^{-1}$/benzyl chloride molar ratio was $4 \times 10^{-3}:1$. After 5 hours, a phenylpyruvic acid selectivity of 75% was obtained. The reaction mixture was treated in the same manner as described above in part 1 of this example. 3. Treatment of the filtrate of part 2 of this example. 1 kg of filtration juice of composition:

| | |
|---|---|
| isopropanol = | 69% w/w |
| $H_2O =$ | 22% |
| $CoCl_2 =$ | 5% |
| organics = | 3.6% | were brought to pH =3 by addition of 22.6 g of 38% HCl. The acidified juices were evaporated continuously in a single-stage evaporator (P =Patm, Tvapors =80° C.). The vaporization rate was 78%.

The distillate was composed of isopropanol/water azeotrope (85/15 w/w). The recovery rate of isopropanol was 99%.

The distillation bottoms decanted in two phases:
organic phase: 47 g.
aqueous phase: 174 g.

The organic phase was burned, and the aqueous phase (saturated in $CoCl_2$) (10) was discarded. 4. Conversion from the calcium phenylpyruvate (CaPP) obtained in part 2 of this example to sodium phenylpyruvate (NaPP)

1. Acidification of the CaPP 0.167 mol of dried calcium phenylpyruvate obtained under the conditions previously described in part 2 of this example was added to a suspension of methyltert-butylether/HCl/$H_2O$ (300 ml/0.67 mol/355 g) in a double-walled reactor stirred by a mixel propeller.

The temperature was maintained at 20° with nitrogen scavenging for 1 hour. The aqueous phase containing the $CaCl_2$ and $CoCl_2$ was decanted. 238.2 g of a slightly yellow organic phase were obtained containing phenylpyruvic acid (PPA) (PPA yield =98%).

2. Salification of PPA to NaPP

The organic phase of phenylpyruvic acid was introduced continuously (200 cm³/h) into a 500-ml reactor stirred by a Rushton propeller. At the same time, a 1.086 sodium solution (w/w) was added continuously to this reactor so as to maintain the pH at 7.5 (20 minutes, nitrogen scavenging).

The NaPP yield on fractions over a reaction period of 4 hours was 95%. The final aqueous layer contained 5% of NaPP in water. The organic layer of methyltert-butylether was directly recycled for acidification.

What is claimed is:

1. A process for the preparation of alkaline phenylpyruvate comprising:
   bringing a suspension of calcium hydroxide in a water/ alcohol mixture into contact with a sulfide, a thiosulfate, an inorganic cobalt salt and carbon monoxide in a reactor;
   introducing benzyl chloride into the resultant mixture while maintaining the reactor under carbon monoxide pressure;
   forming calcium phenylpyruvate oxidizing the cobalt;
   filtering the calcium phenylpyruvate;
   drying the calcium phenylpyruvate at a temperature effective to eliminate the alcohol;
   acidifying a suspension of the calcium phenylpyruvate in a water-immiscible organic solvent;
   isolating the acidified phenylpyruvate; and
   neutralizing the acid phenylpyruvate with an alkaline base.

2. The process of claim 1, wherein the cobalt concentration is from about $1 \times 10^{-3}$ to $5 \times 10^{-3}$ mole/liter.

3. The process of claim 1, wherein the combined quantity of the sulfide and thiosulfate expressed in moles per gram-atom of cobalt is from about 0.01:1 to 1:1.

4. The process of claim 1, wherein the molar quantity of cobalt catalyst per mole of benzyl chloride is from about $1 \times 10^{-3}:1$ to $1 \times 10^{-2}:1$.

5. The process of claim 1, wherein the carbon monoxide pressure is from about 5 to 30 bar.

6. The process of claim 1, wherein the temperature of the reaction is from about 60° to 90° C.

7. The process of claim 1, wherein the oxidation of the cobalt catalyst is carried out by addition of sodium hypochlorite.

8. The process of claim 7, wherein the sodium hypochlorite is added at a temperature of about 60° C.

9. The process of claim 7, wherein the sodium hypochlorite is a 10% aqueous solution of sodium hypochlorite.

10. The process as claimed in claim 1, wherein the filtration step is carried out with a thin-layer filter.

11. The process of claim 1, further comprising washing the residue of the filtration step with a water/alcohol mixture of the same nature as used in the contacting step.

12. The process of claim 1, further comprising acidifying the filtrate of the filtration step, distilling a water-/alcohol azeotropic mixture from said filtrate and recycling said azeotropic mixture for use in the contacting step.

13. The process of claim 1, wherein the alcohol of the water/alcohol mixture is isopropanol.

14. The process of claim 12, wherein the acidification of the filtrate is carried out up to a pH of 3.

15. The process of claim 1, wherein the water-immiscible organic solvent is a halogenated or non-halogenated aliphatic or aromatic hydrocarbon, an ether or an ester.

16. The process of claim 15, wherein the aliphatic or aromatic hydrocarbon is selected from the group consisting of chloroform, methylene chloride, chlorobenzene, toluene and xylene.

17. The process of claim 15, wherein the ether is selected from the group consisting of isopropyl ether, ethyl ether and methyltert-butylether.

18. The process of claim 15, wherein the ester is ethyl acetate.

19. The process of claim 1, wherein the water-immiscible solvent is methyltert-butylether.

20. The process of claim 1, wherein the acidification of the suspension is carried out with a solution of hydrochloric acid having a molar ratio of hydrochloric acid to phenylpyruvate of from about 2:1 to 8:1.

21. The process of claim 20, wherein the molar ratio of hydrochloric acid to phenylpyruvate is about 4:1.

22. The process of claim 1, wherein the isolation of the acidified phenylpyruvate is carried out by decantation.

23. The process of claim 1, wherein said inorganic cobalt salt is a cobalt chloride.

24. The process of claim 23, wherein said cobalt chloride is cobalt dichloride.

25. The process of claim 1, wherein the temperature of the drying step is less than or equal to 80° C.

* * * * *

UNITED STATES PATENT AND TRADEMARK OFFICE
CERTIFICATE OF CORRECTION

PATENT NO. : 4,997,979
DATED : March 5, 1991
INVENTOR(S) : Phillippe Coste et al.

It is certified that error appears in the above-identified patent and that said Letters Patent is hereby corrected as shown below:

Title page;

Item [75] Inventors, line 1, "Phillippe" should read --Philippe--.

Item [57] ABSTRACT, line 2, "benxzyl" should read --benzyl--.

Claim 1, column 6, line 32, "forming calcium phenylpyruvate oxidizing the co-" should read --forming calcium phenylpyruvate;-- column 6, line 33, "balt;" should read --oxidizing the cobalt;--

Signed and Sealed this

Twenty-second Day of June, 1993

Attest:

MICHAEL K. KIRK

Attesting Officer

Acting Commissioner of Patents and Trademarks